(12) United States Patent
Bikker et al.

(10) Patent No.: US 8,852,883 B2
(45) Date of Patent: Oct. 7, 2014

(54) RAPID FRET-BASED DIAGNOSIS OF BACTERIAL PATHOGENS

(75) Inventors: Floris Jacob Bikker, Gouda (NL); Wendy Esmeralda Kaman-Van Zanten, 's-Gravenzande (NL)

(73) Assignee: Nederlandse Organisatie voor toegepast-natuurwetenschappelijk onderzoek TNO, Delft (NL)

( * ) Notice: Subject to any disclaimer, the term of this patent is extended or adjusted under 35 U.S.C. 154(b) by 436 days.

(21) Appl. No.: 13/130,213

(22) PCT Filed: Nov. 19, 2009

(86) PCT No.: PCT/NL2009/050702
§ 371 (c)(1),
(2), (4) Date: Oct. 3, 2011

(87) PCT Pub. No.: WO2010/059051
PCT Pub. Date: May 27, 2010

(65) Prior Publication Data
US 2012/0021454 A1 Jan. 26, 2012

(30) Foreign Application Priority Data

Nov. 20, 2008 (EP) .................................... 08169548
May 20, 2009 (EP) .................................... 09160815

(51) Int. Cl.

| | | |
|---|---|---|
| C12Q 1/04 | (2006.01) | |
| A61K 38/04 | (2006.01) | |
| C07K 5/00 | (2006.01) | |
| C07K 7/00 | (2006.01) | |
| C07K 16/00 | (2006.01) | |
| C07K 17/00 | (2006.01) | |
| A61K 38/06 | (2006.01) | |
| C09B 29/00 | (2006.01) | |
| C07K 5/02 | (2006.01) | |
| C07K 5/06 | (2006.01) | |
| C07K 5/08 | (2006.01) | |
| C07K 5/062 | (2006.01) | |
| C07K 7/06 | (2006.01) | |
| C12Q 1/37 | (2006.01) | |
| C07K 5/103 | (2006.01) | |

(52) U.S. Cl.
CPC .............. *C07K 7/06* (2013.01); *G01N 2333/32* (2013.01); *G01N 2333/21* (2013.01); *C07K 5/0207* (2013.01); *C07K 5/06* (2013.01); *C07K 5/08* (2013.01); *C07K 5/06043* (2013.01); *G01N 2333/954* (2013.01); *C12Q 1/37* (2013.01); *C12Q 1/04* (2013.01); *G01N 2333/952* (2013.01); *C07K 5/1013* (2013.01)
USPC ............. 435/34; 530/329; 530/330; 530/331; 534/851

(58) Field of Classification Search
None
See application file for complete search history.

(56) References Cited

U.S. PATENT DOCUMENTS

2005/0142622 A1 6/2005 Sanders et al.

FOREIGN PATENT DOCUMENTS

| WO | WO8000351 A1 | 3/1980 |
|---|---|---|
| WO | WO 8000351 A1 * | 3/1980 |
| WO | WO 9740065 A2 * | 10/1997 |
| WO | WO9740065 A2 | 10/1997 |
| WO | WO9837226 A1 | 8/1998 |
| WO | WO0159149 A2 | 8/2001 |
| WO | WO2007136436 A2 | 11/2007 |

OTHER PUBLICATIONS

White et al "A Continuous Fluorometric Assay for Leukotriene D4 Hydrolase" Anal Biochem 268:245-251. Published 1999.*
Rasooly et al "Detection of botulinum neurotoxin-A activity in food by peptide cleavage assay" Intl J Food Microbiol 126:135-139. Published Aug. 15, 2008.*
PCT/NL2009/050702 International Search Report and Written Opinion, 24 pages, Jun. 29, 2010.
McCallum, Christine D. et al. "Tissue factor positions and maintains the factor VIIa active site far above the membrane surface even in the absence of the factor VIIa Gla domain: A fluorescence resonance energy transfer study" Journal of Biological Chemistry, vol. 272, No. 48, Nov. 28, 1997, pp. 30160-30166, XP002526365.
Rasooly, Reuven et al. "Detection of botulinum neurotoxin-A activity in food by peptide cleavage assay" International Journal of Food Microbiology, vol. 126, Aug. 15, 2008, pp. 135-139, XP023315608.
White I J et al. "A continuous fluorometric assay for leukotriene D4 hydrolase" Analytical Biochemistry, vol. 268, No. 2, Mar. 15, 1999, pp. 245-251, XP7912861.

(Continued)

*Primary Examiner* — Maury Audet
*Assistant Examiner* — Zachary J Miknis
(74) *Attorney, Agent, or Firm* — Fish & Richardson P.C.

(57) ABSTRACT

Substrates for detecting microorganisms are provided, wherein the substrate comprises a set of molecular markers linked, optionally with linker molecules or moieties, to a di-, or tripeptide consisting of amino acids X1 and X2, or X1, X2 and X3, in which one of them, for example, X1, is a D-amino acid and the others, for example, X2 and X3, may be any D- or L-amino acid. The substrate preferably is used for the detection of *Bacillus anthracis*. Also provided are substrates for detecting *Pseudomonas aeruginosa*, wherein the substrate comprises a set of molecular markers linked, optionally with linker molecules or moieties to a tri-, tetra-, or pentapeptide consisting of glycine amino acids. The invention further comprises methods for detecting microorganisms, specifically *B. anthracis* and *P. aeruginosa*, with the substrates of the invention and use of the substrate(s) in such a method.

11 Claims, 19 Drawing Sheets

(56) References Cited

OTHER PUBLICATIONS

Elston, Caroline et al. "New continuous and specific fluorometric assays for *Pseudomonas aeruginosa* elastase and LasA protease" Analytical Biochemistry, vol. 368, No. 1, Jul. 18, 2007, pp. 87-94, XP022156835.

Warfield, Rachel et al. "Internally quenched peptides for the study of lysostaphin: an antimicrobial protease that kills *Staphylococcus aureus*" Organic & Biomolecular Chemistry, vol. 4, Jan. 1, 2006, pp. 3626-3638, XP007912850.

Vessillier, Sandrine et al. "Capillary electrophoresis in the assay of the hydrolysis of glycine-containing peptides by a protease from *Pseudomonas aeruginosa*" Journal of Chromatography, vol. 776, No. 1, Jul. 25, 1997, pp. 133-137, XP004086107.

\* cited by examiner

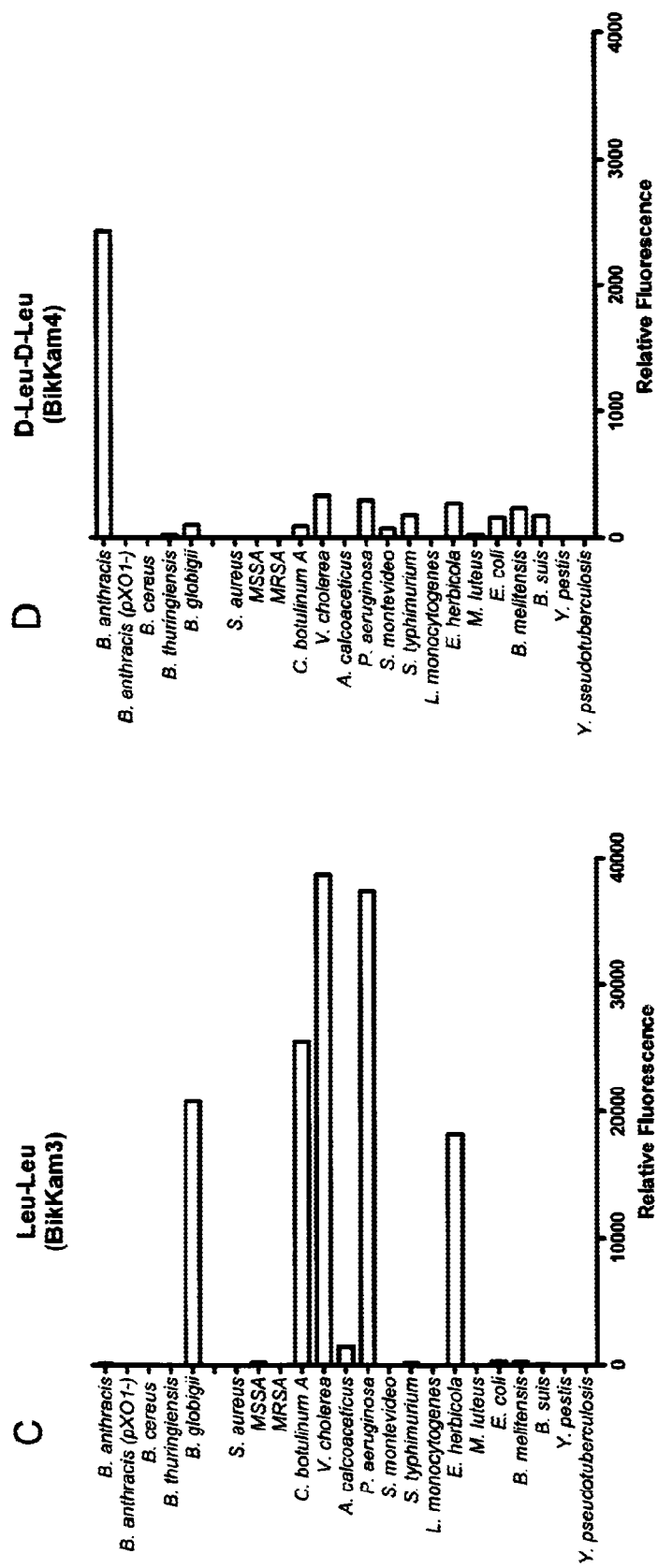
Fig. 1, contd.

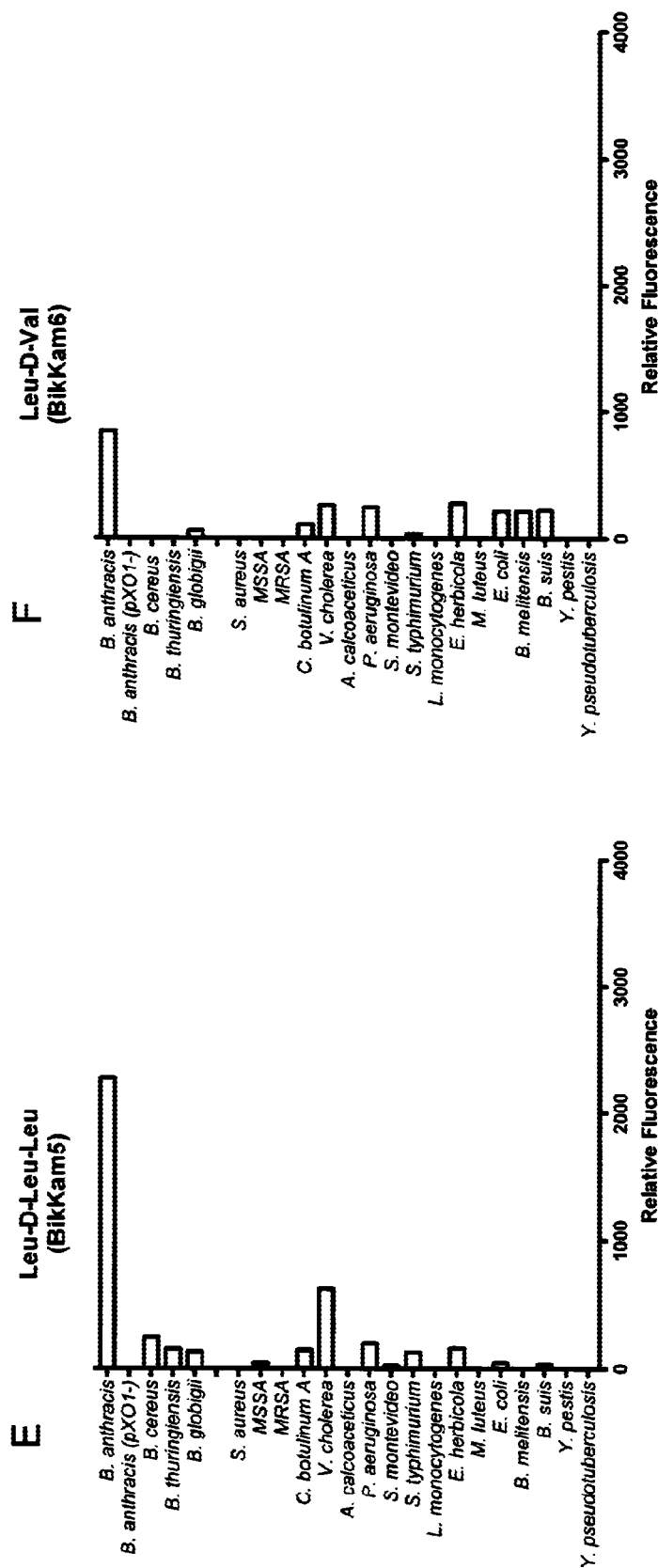
Fig. 1, contd.

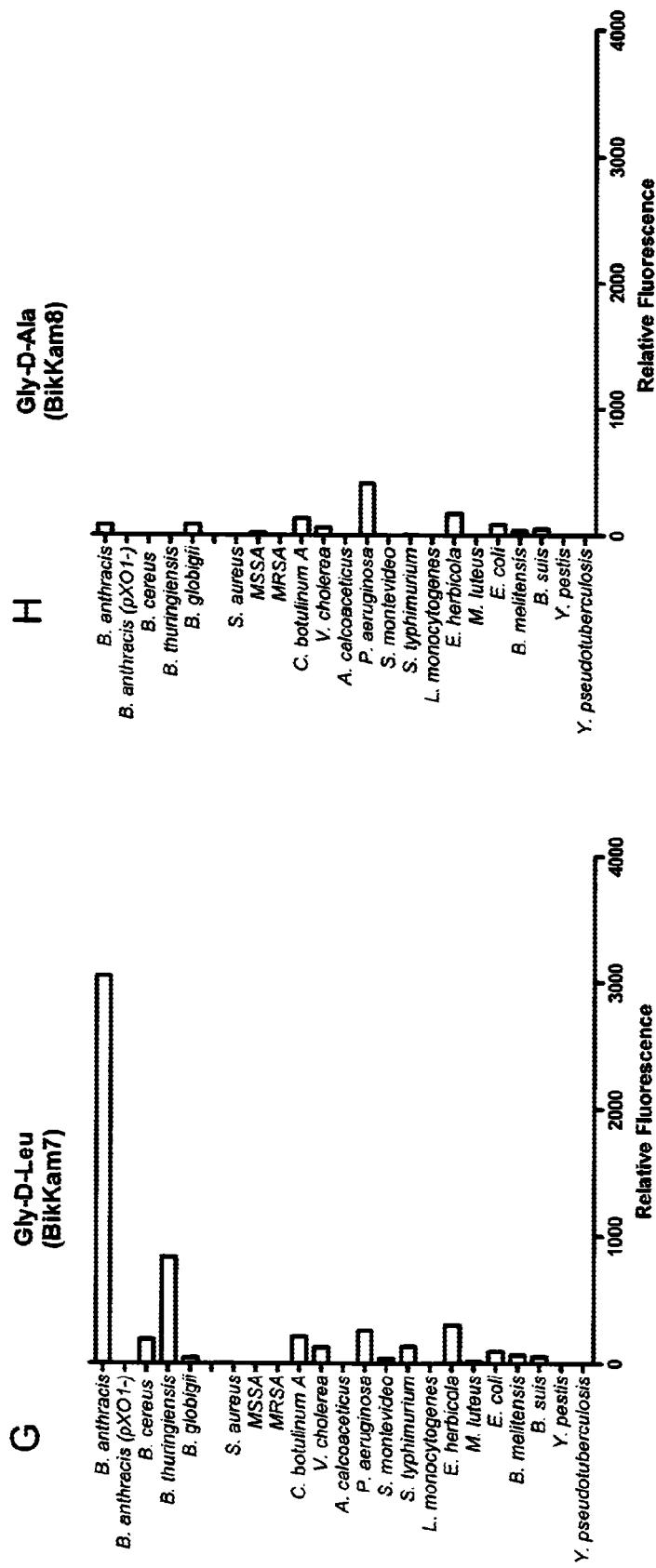
Fig. 1, contd.

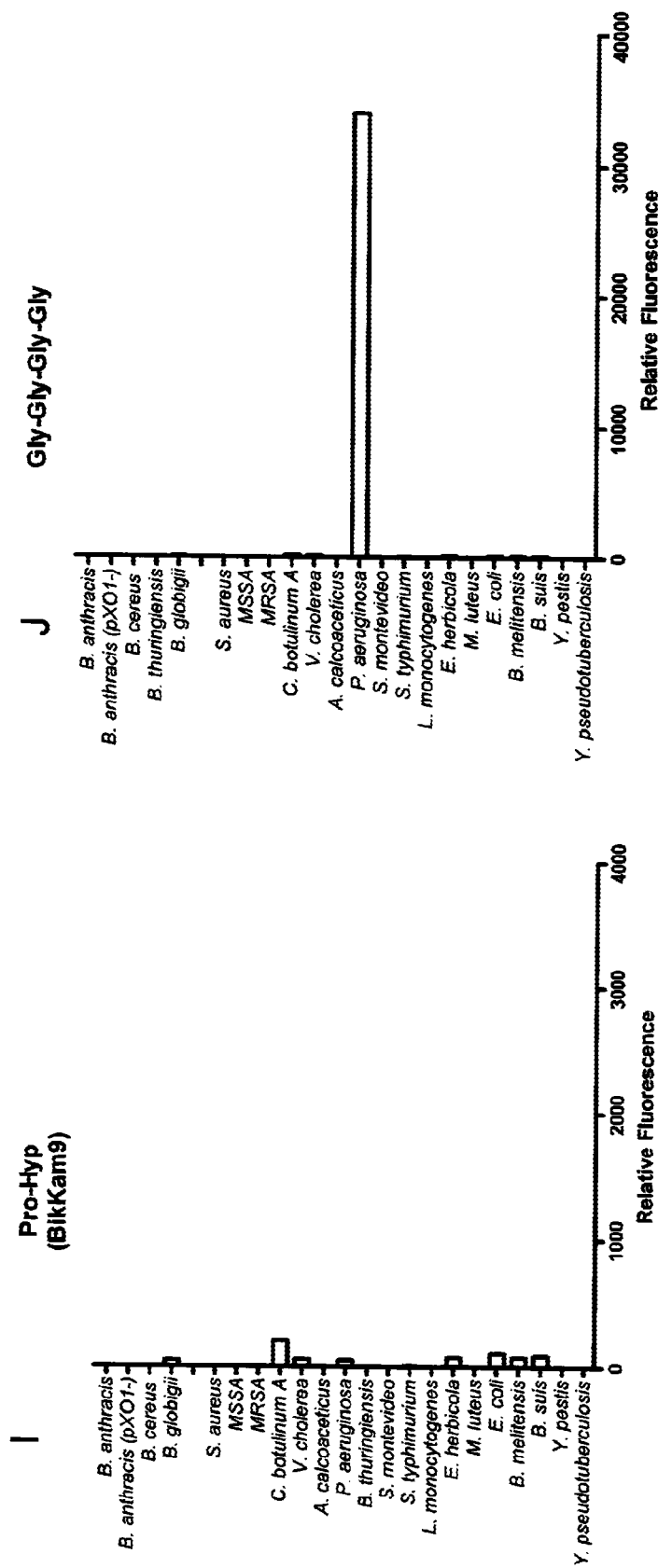
Fig. 1, contd.

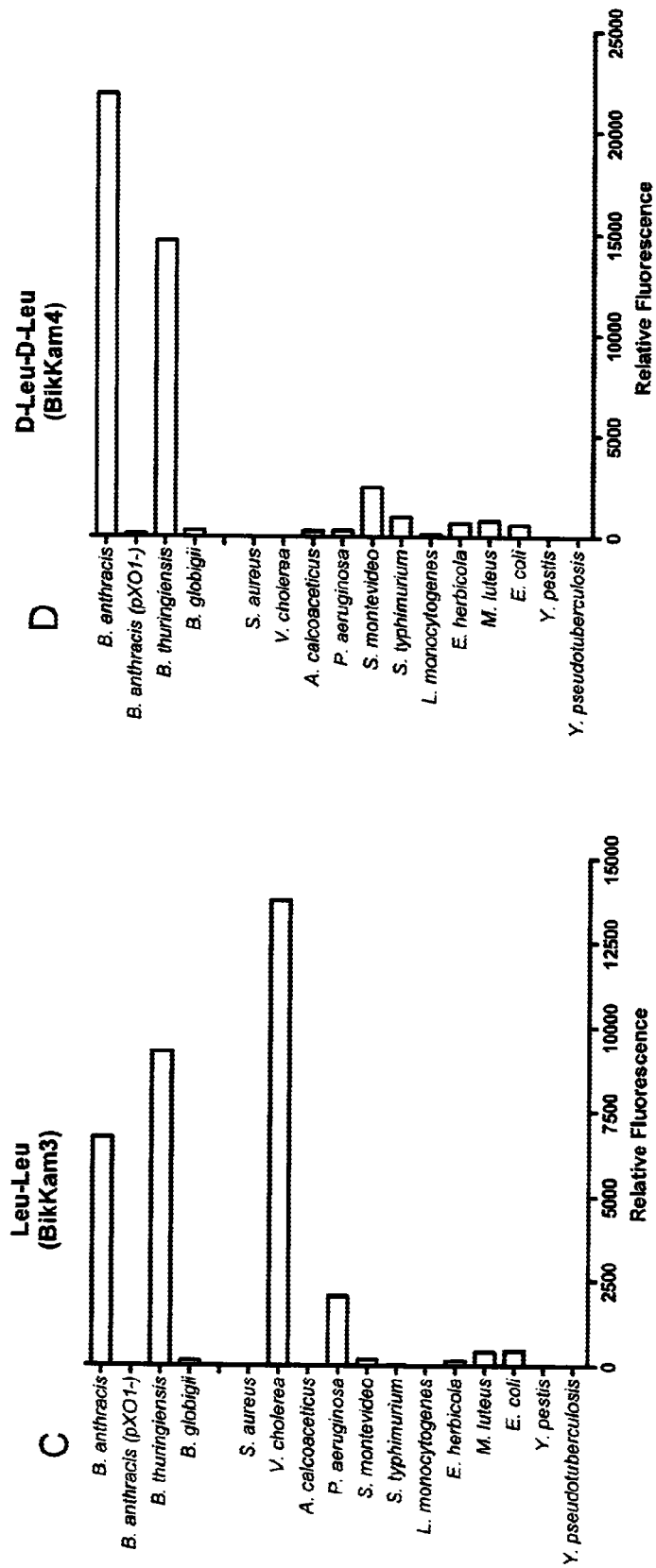
Fig. 3, contd.

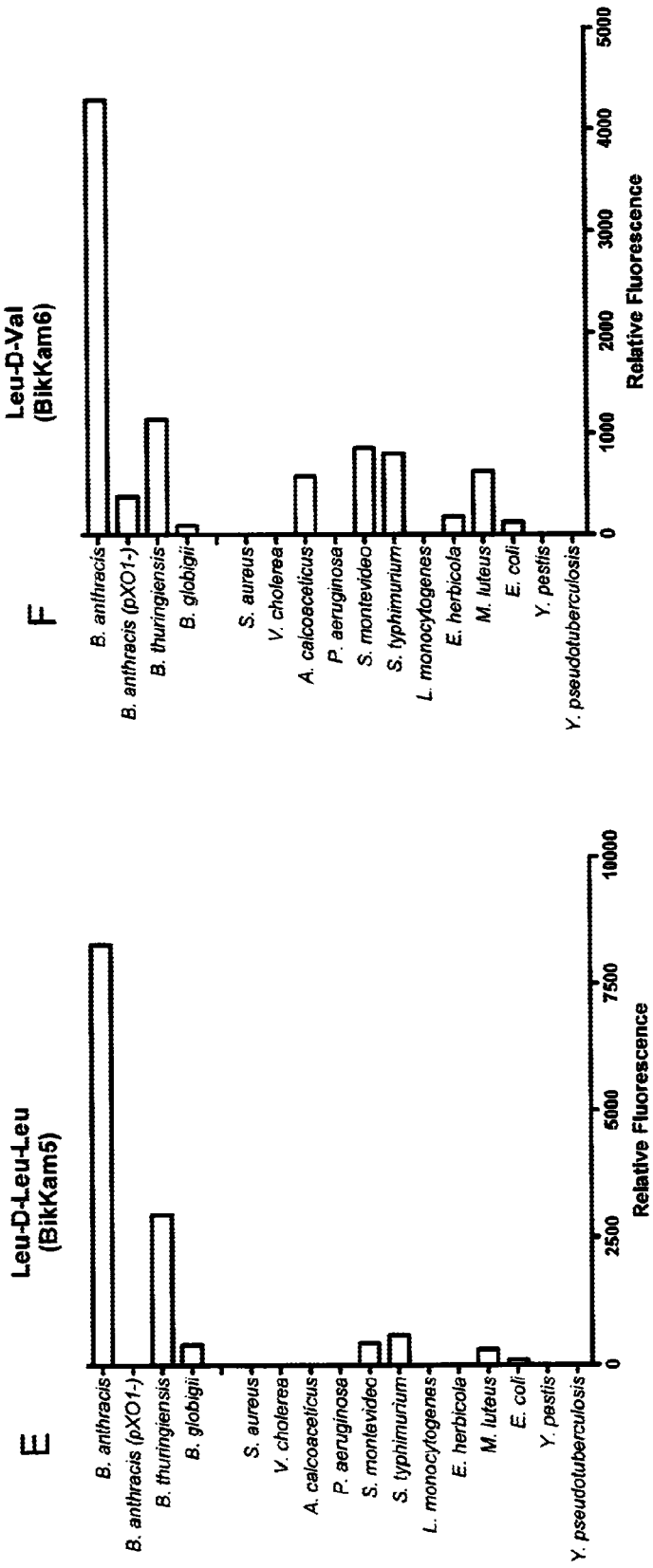
Fig. 3, contd.

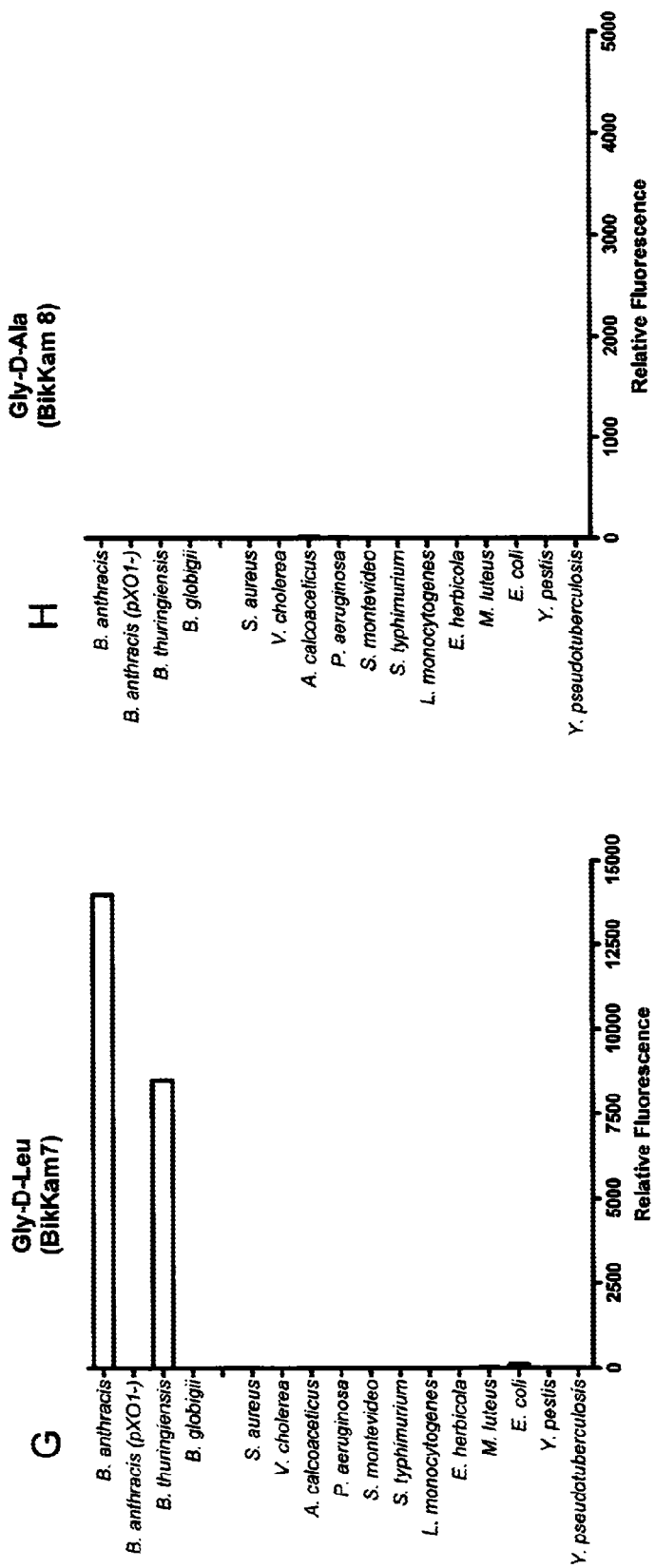
Fig. 3, contd.

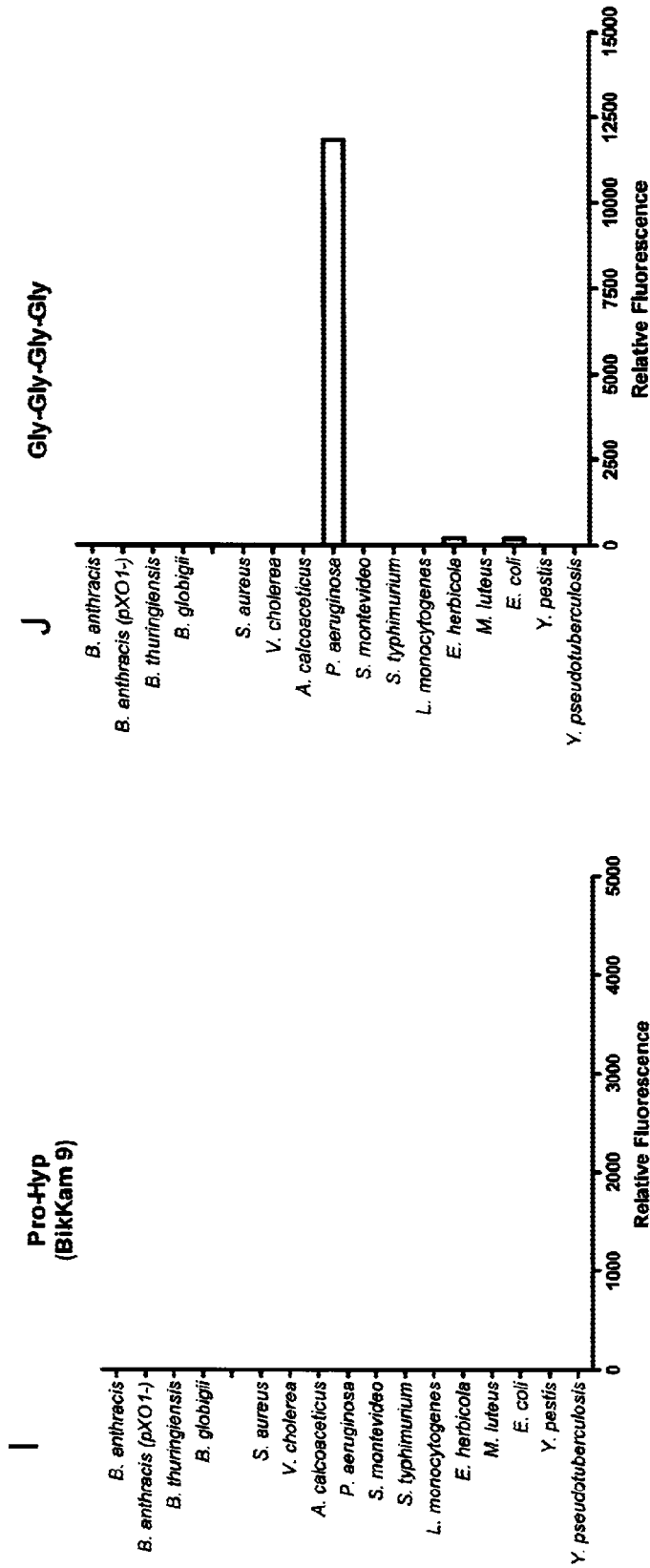
Fig. 3, contd.

RAPID FRET-BASED DIAGNOSIS OF BACTERIAL PATHOGENS

CROSS REFERENCE TO RELATED APPLICATIONS

This application is a U.S. National Phase Application under 35 U.S.C. §371 of International Application PCT/NL2009/050702, filed on Nov. 19, 2009, which claims the benefit of European Application No. 08169548.8, filed on Nov. 20, 2008 and European Application No. 09160815.8, filed on May 20, 2009, the entire contents of each of which are hereby incorporated by reference in their entireties.

FIELD OF THE INVENTION

The present invention is in the field of diagnostics, more specifically detection of hazardous compounds or organisms, more specifically detection of micro-organisms, more specifically anthrax (*Bacillus anthracis*) and *Pseudomonas aeruginosa*.

BACKGROUND

*Pseudomonas aeruginosa* is a bacterial pathogen which causes infections of the pulmonary tract, urinary tract, burns, wounds, and also causes other blood infections. It is the most common cause of infections of burn injuries and of the external ear (otitis externa), and is the most frequent colonizer of medical devices (e.g., catheters). *Pseudomonas* can, in rare circumstances, cause community-acquired pneumonias, as well as ventilator-associated pneumonias, being one of the most common agents isolated in several studies. One in ten hospital-acquired infections are from *Pseudomonas*.

Detection of *P. aeruginosa* in clinical settings is still mostly performed by culturing sample bacteria on selective plates or based on immunological tests comprising antibodies to surface antigens of the bacterium, such as outer polysaccharide matrices. Rapid diagnosis and detection is important to start suitable therapy and to control the spread of the bacterium.

Anthrax is a zoonotic disease caused by the spore-forming bacterium *Bacillus anthracis*. *B. anthracis* spores remain viable in the environment for years, representing a potential source of infection. Anthrax occurs in humans in three clinical forms: inhalational, gastrointestinal, and cutaneous. Inhalational anthrax results from aerosolization of *B. anthracis* spores through industrial processing or intentional release. Gastrointestinal or oropharyngeal forms of the disease result from ingestion of infected undercooked or raw meat. Cutaneous anthrax is the most common type of naturally acquired anthrax infection and usually occurs after skin contact with contaminated products from infected animals. Historically, the case-fatality rate for cutaneous anthrax has been <1% with antibiotic treatment and 20% without antibiotic treatment (Brachman P. S. and Kaufmann A. F. In: Evans A. S., Brachman P. S., eds. Bacterial infections of humans. New York: Plenum Medical Book Company, 1998:95-111; Dixon T. C. et al, N. Engl. J. Med. 1999;341:815-26). Case-fatality rates for inhalational anthrax are high, even with appropriate antibiotics and supportive care (Jernigan J. A., et al. Emerg. Infect. Dis. 2001;7:933-44). Among the 18 cases of inhalational anthrax identified in the United States during the 20$^{th}$ century, the overall case-fatality rate was >75%. After the biologic terrorism attack in fall 2001 in which *B. anthracis* spores were released through the mail, the case-fatality rate for patients with inhalational anthrax was 45% (5 of 11 cases) (Jernigan D. B., et al., Emerg. Infect. Dis. 2002;8:1019-28).

The incubation period for anthrax is usually <2 weeks; however, because of spore dormancy and slow clearance from the lungs, the incubation period for inhalational anthrax can be prolonged for months. This phenomenon of delayed onset has not been recognized for cutaneous or gastrointestinal exposures. Discharges from cutaneous lesions are potentially infectious, but person-to-person transmission has been reported rarely. Person-to-person transmission of inhalational anthrax has not been documented.

*B. anthracis* is one of the biologic agents most likely to be used as a weapon because 1) its spores are highly stable; 2) the spores can infect through the respiratory route; and 3) the resulting inhalational disease has a high case-fatality rate. In 1979 an unintentional release of *B. anthracis* spores from a military microbiology facility in the former Soviet Union resulted in 69 deaths (Meselson M., et al. Science 1994;266: 1202-8). The anthrax outbreak after *B. anthracis* spores were distributed through the U.S. mail system in 2001 further underscores the dangers of this organism as a terrorist threat.

After a terrorist attack, exposures to *B. anthracis* spores can occur through primary and secondary aerosols. Primary aerosols are dispersions of particles in air resulting from a biologic agent's initial release, whether through a disseminating device or through handling of an agent-containing package (e.g., in mechanical processing of mail). Secondary aerosols result from disruption and resuspension of settled particles.

Many detection systems for the presence of anthrax have been proposed. Archaic technologies such as staining have nowadays been replaced by more reliable molecular diagnostics, such as PCR (e.g. Makino, S. T. et al., J. Clin. Microbiol. 31:547-51, 1993); U.S. Pat. No. 6,884,588; Qiagen's Real-Art™ *B. anthracis* PCR) and immunoassays (e.g. Swiecki, M. K., et al. J. Immunol. 176:6076-84, 2006; U.S. Pat. No. 6,828,110; Response Medical Corp.'s RAMP™ Anthrax Assay). However, many of these systems can not differentiate between virulent and avirulent strains of *Bacillus anthracis*. The virulence of anthrax is mainly given by the presence of the pXO1 plasmid, on which plasmid the gene for the toxic proteins of anthrax are situated, of which one is denominated the lethal factor (LF-protein).

A relatively novel, very robust and highly reliable technology for the visualization of biological material is the FRET (Fluorescent Resonance Energy Transfer) technology. In this process, a photon from an energetically excited fluorophore, the 'donor', raises the energy state of an electron in another molecule, the 'acceptor', to higher vibrational levels of the excited state. As a result, the energy level of the donor fluorophore returns to the ground state, without emitting fluorescence. The acceptor thus functions as a quencher of the fluorescence. This mechanism is limited by the distance between the donor and the acceptor molecule. Typical effective distances between the donor and acceptor molecules are in the 10 to 100 Å range, which makes them useful in molecular diagnostics of e.g. nucleic acids and proteins.

The FRET technology has been used to detect *Bacillus anthracis* through coupling of FRET components to nucleic acids, especially those resulting from PCR products (Qi Y. et al., Appl. Environm. Microbiol. 67:3720-7, 2001; Patra G., et al., Annal. New York Acad. Sci. 969:106-11, 2002; Mathur, N. et al., J. Sensors 2008, Art. ID #270475). However, using FRET in combination with PCR still requires a high skill level of the technician performing the assay. Recently, FRET technology has been applied for the detection of anthrax through the proteolytic characteristics of the lethal factor protein (LF). In this assay a labeled substrate was added to the sample which is cleavable by LF (Cummings, R. T. et al., Proc. Natl.

Acad. Sci. USA 99:6603-6, 2002). However, this assay gives rise to false positive signals since the cleavage characteristics for the substrate are not specific.

For *P. aeruginosa* a FRET based system has been described based on DNA (Mancini, n. et al., 2009, J. Clin. Microbiol. doi:10.1128/JCM.00011-09). However, in this assay a DNA lysing step and a PCR step should be performed in order to provide sufficient DNA.

Thus there is still need for an improved detection system for pathogenic microorganisms such as *B. anthracis* and *P. aeruginosa.*

SUMMARY OF INVENTION

Technical Problem

The problem to be solved by the present invention is to provide the specific detection and diagnosis of pathogenic microorganisms, more specifically *B. anthracis* and *P. aeruginosa* in situ.

Solution to Problem

The invention comprises substrates for detection, diagnosis, or identification of micro-organisms, preferably *B. anthracis*, or their enzymes, wherein said wherein said substrate comprises a set of molecular markers linked, optionally with linker molecules or moieties, to a di-, or tripeptide consisting of amino acids X1and X2, or X1, X2 and X3, in which one of them, for example X1, is a D-amino acid and the others, for example X2 and X3, may be any D- or L-amino acid. In such a substrate preferably the D-amino acid is a neutral amino acid, preferably DLeu, DVal, DIle, DGly or DAla, more preferably DLeu, DVal or DIle. Further preferred is an embodiment wherein the L-amino acid or one of the two L-amino acids is Leu. Also preferred is a substrate for fluorescent detection of *Bacillus anthracis* according to the invention, wherein said set of molecular markers comprises a fluorescent label, preferably FITC (fluorescein-5-isothiocyanate), and a quencher for said fluorescent label, preferably DABCYL (4-((-4-(dimethylamino)-phenyl)-azo)-benzoic acid). In this case preferably the linkers are aminohexanoic acid (for FITC) and lysine (for DABCYL). In this case, the substrate may be defined as: FITC-Ahx-X1-X2-X3-Lys-DABCYL wherein X1, X2 and X3 are as defined as above, wherein X3 may be absent and wherein Lys stands for Lysine, and Ahx stands for aminohexanoic acid. More specifically, the substrate of the invention is chosen from the group consisting of:

FITC-Ahx-Leu-DLeu-Lys-DABCYL,

FITC-Ahx-DLeu-Leu-Lys-DABCYL,

FITC-Ahx-DLeu-DLeu-Lys-DABCYL,

FITC-Ahx-Leu-DLeu-Leu-Lys-DABCYL,

FITC-Ahx-Leu-DVal-Lys-DABCYL,
and

FITC-Ahx-Gly-DLeu-Lys-DABCYL.

In another embodiment, in said substrate according to the invention said set of molecular markers comprises two terminal acetylated cysteines and the linkers are absent. In this case, preferably said substrate is:

AcNH-Cys(S-Ac)-X1-X2-X3-Cys(S-Ac)-OH, wherein X1, X2 and X3 are as defined as above, wherein X3 may be absent and wherein Cys(S-Ac) stands for thiol acetylated cysteine and AcNH for an acetylated amino terminus. More preferably, said substrate is chosen from the group consisting of:

AcNH-Cys(S-Ac)-Leu-DLeu-Cys(S-Ac)-OH,

AcNH-Cys(S-Ac)-DLeu-Leu-Cys(S-Ac)-OH,

AcNH-Cys(S-Ac)-DLeu-DLeu-Cys(S-Ac)-OH,

AcNH-Cys(S-Ac)-Leu-DLeu-Leu-Cys(S-Ac)-OH,

AcNH-Cys(S-Ac)-Leu-DVal-Cys(S-Ac)-OH,
and

AcNH-Cys(S-Ac)-Gly-DLeu-Cys(S-Ac)-OH.

In another embodiment, the invention comprises a method for the detection of micro-organisms, in particular *Bacillus anthracis* in a sample comprising adding a substrate as defined above to the sample and detecting fluorescence or shift in color. In a specific embodiment, the fluorescent signal is located intracellularly in the microbial cells. In a further embodiment, the sample is chosen from a body fluid, powder, water, food, medium or any other biological matrix.

More specifically, the invention relates to a method for the identification of *Bacillus anthracis*$^{PXO1+}$ in a sample comprising adding a substrate as defined above to the sample and detecting fluorescence, shift in color or a specific mass spectrum, or achieve detection by capillary electrophoresis.

The invention further comprises the use of the substrate as defined above for the detection and diagnosis of *Bacillus anthracis.*

In a yet other embodiment the invention comprises a substrate for detection of micro-organisms, more specifically *P. aeruginosa*, wherein said substrate comprises a set of molecular markers linked, optionally with linker molecules or moieties to a tri-, tetra-, or pentapeptide consisting of glycine amino acids. More preferably, said set of molecular markers comprises a fluorescent label, preferably FITC (fluorescein-5-isothiocyanate), and a quencher for said fluorescent label, preferably DABCYL (4-((-4-(dimethylamino)-phenyl)-azo)-benzoic acid). With these markers, the linkers preferably are aminohexanoic acid (for FITC) and lysine (for DABCYL). Most preferred in this respect are the substrates chosen from the group consisting of:

FITC-Ahx-Gly-Gly-Gly-Gly-Gly-Lys-DABCYL,

FITC-Ahx-Gly-Gly-Gly-Gly Lys-DABCYL,

FITC-Ahx-Gly-Gly-Gly-Lys-DABCYL,

AcNH-Cys(S-Ac)-Gly-Gly-Gly-Gly-Gly-Cys(S-Ac)-OH,

AcNH-Cys(S-Ac)-Gly-Gly-Gly-Gly-Cys(S-Ac)-OH,
and

AcNH-Cys(S-Ac)-Gly-Gly-Gly-Cys(S-Ac)-OH.

The invention further comprises a method for the detection of micro-organisms, in particular *Pseudomonas aeruginosa* in a sample comprising adding a substrate as defined above to the sample and detecting fluorescence or shift in color. The invention also provides this method wherein the fluorescent signal is located intracellularly in the microbial cells. Preferably in these methods the sample is chosen from a body fluid, powder, water, food, medium or any other biological matrix. Further, the invention relates to the use of a substrate according as defined above for the detection and diagnosis of *Pseudomonas aeruginosa*.

Advantageous Effects of Invention

First of all the invention offers a quick and efficient way of specifically detecting micro-organisms and specifically anthrax in a sample. Moreover, it is discriminative for anthrax that carries the PXO1 plasmid, i.e. anthrax that is virulent. Further, the detection method can be used in any sample with anthrax, without the need of (pre)-isolation.

DESCRIPTION OF EMBODIMENTS

Figure 1:
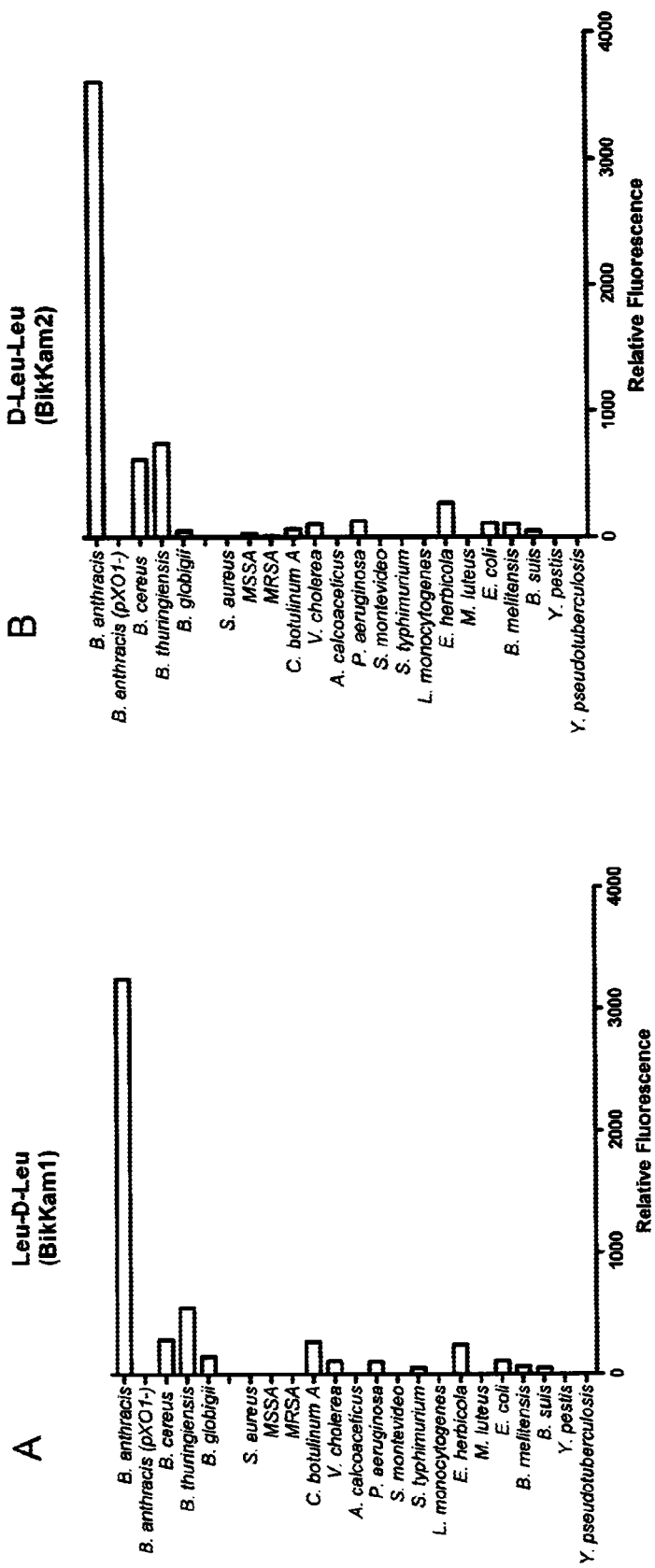
FIG. 1. Fluorescent signal of FRET after 60 minutes of invented substrates by enzymes of bacteria grown in bacterial growth medium (BHI) (in vitro)
A: BikKam1 is specifically cleaved by a (virulent) *B. anthracis*-derived enzyme.
B: BikKam2 is specifically cleaved by a (virulent) *B. anthracis*-derived enzyme. A weak signal was observed for *B. cereus* and *B. thuringiensis*.
C: *B. anthracis*-derived enzymes do not digest BikKam3. Otherwise enzymes derived from *B. globigii, C. botulinum, P. aeruginosa, V. cholerae* and *E. herbicola* show activity on the substrate, indicating that the enzymes, more specifically, this approach, enables broad-spectrum detection of micro-organisms (see also FIG. 3C).
D: BikKam4 is specifically cleaved by a (virulent) *B. anthracis*-derived enzyme.
E: BikKam5 is specifically cleaved by a (virulent) *B. anthracis*-derived enzyme. Some cleavage is observed for *V. cholerae* as well.
F: BikKam6 is relatively moderate, but specifically cleaved by a (virulent) *B. anthracis*-derived enzyme.
G: BikKam7 is specifically cleaved by a (virulent) *B. anthracis*-derived enzyme. A weak signal was observed for *B. thuringiensis*.
H. No significant enzyme activity could be measured using BikKam8 with the currently used micro-organisms.
I. No significant enzyme activity could be measured using BikKam9 with the currently used micro-organisms.
J: FITC-Ahx-Gly-Gly-Gly-Gly -Lys-DABCYL is specifically cleaved by a *P. aeruginosa*-derived enzyme.
Figure 2:
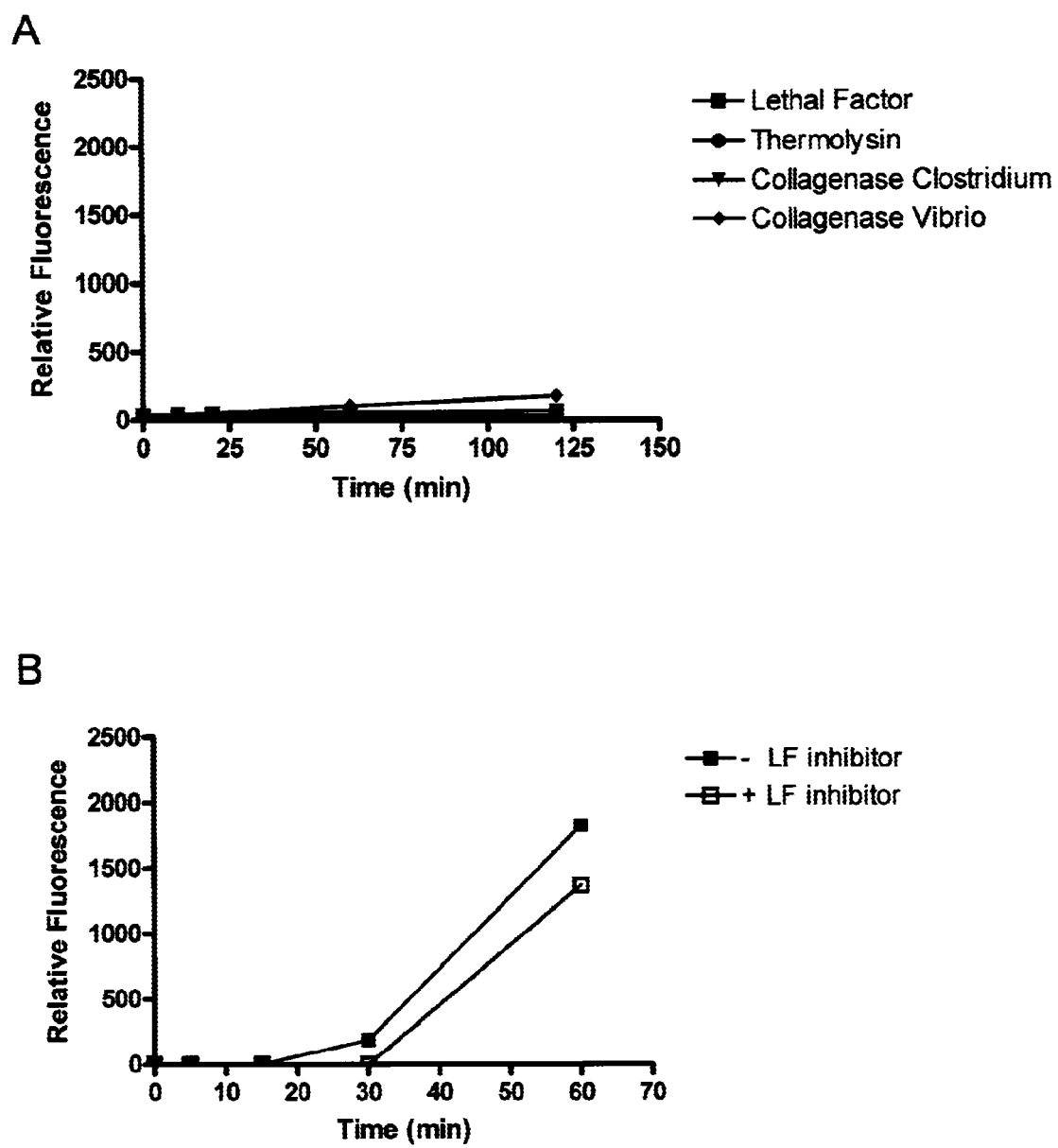
FIG. 2. The enzyme that cleaves BikKam1 is situated on the PXO1 plasmid, but is not Lethal Factor.
A: Substrate BikKam1 was added to several purified enzymes: Lethal Factor, thermolysin, collegase (from *Clostridium* sp.) and collegenase (from *Vibrio* sp). No signal with all enzymes was observed, underlining the specificity of BikKam1 for a *B. anthracis*-derived enzyme, but which is not LF.
B: BikKam1 was added to LF. Supplemented LF inhibitor did not result in a significant decrease of substrate cleavage, underlining the specificity of BikKam1 for a *B. anthracis*-derived enzyme, but which is not LF.
Figure 3:
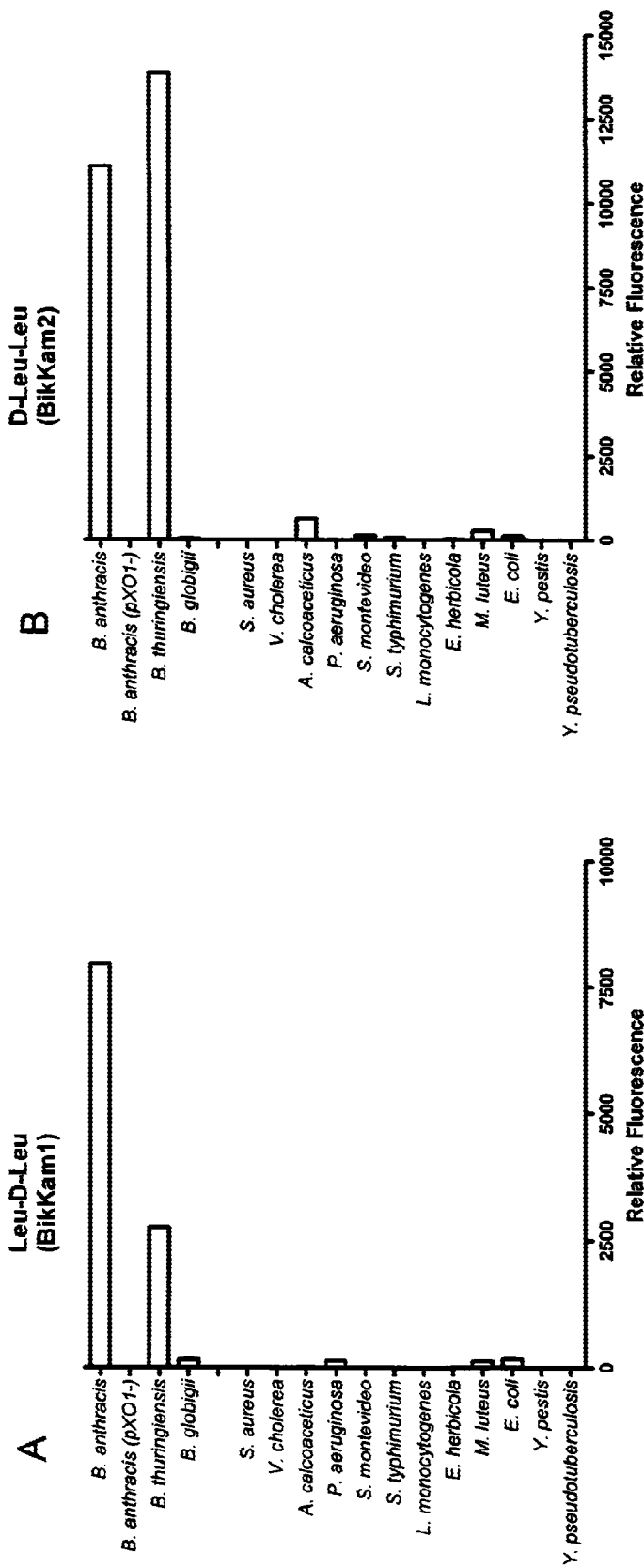
FIG. 3. Fluorescent signal of FRET after 60 minutes of incubation of substrates with enzymes of bacteria grown in human serum (ex vivo),
A: BikKam1 is specifically cleaved by a (virulent) *B. anthracis*-derived enzyme. Some weak activity was observed for *B. thuringiensis* as well.
B: BikKam2 is specifically cleaved by a (virulent) *B. anthracis*-derived enzyme and a *B. thuringiensis*-derived enzyme.
C: BikKam3 is specifically cleaved by a (virulent) *B. anthracis*-derived enzyme, a *B. thuringiensis*-derived enzyme and a *V. cholerae*-derived enzyme. Some weak activity was observed for *P. aeruginosa*. These data provide evidence for differential use of the invented substrates /approach; identical substrates show differential activity when grown in either BHI or Human serum (compare with FIG. 1C).
D: BikKam4 is specifically cleaved by a (virulent) *B. anthracis*-derived enzyme and a *B. thuringiensis*-derived enzyme.
E: BikKam5 is specifically cleaved by a (virulent) *B. anthracis*-derived enzyme. Some weak activity was observed for *B. thuringiensis*.
F: BikKam6 is moderately specifically cleaved by a (virulent) *B. anthracis*-derived enzyme. Some weak background with other bacteria was observed at 60 min. Measurements at earlier time points e.g. 30 minutes hardly revealed any background with bacteria other than (virulent) *B. anthracis* (not shown).
G: BikKam7 is specifically cleaved by a (virulent) *B. anthracis*-derived enzyme and to a lesser extend by a *B. thuringiensis*-derived enzyme.
H. No significant enzyme activity could be measured using BikKam8 with the currently used micro-organisms.
I. No significant enzyme activity could be measured using BikKam9 with the currently used micro-organisms.
J: FITC-Ahx-Gly-Gly-Gly-Gly-Lys-DABCYL is specifically cleaved by a *P. aeruginosa*-derived enzyme.

The current invention is directed to a method for the detection or diagnosis of anthrax based on an interaction between a substrate and a proteolytic enzyme that is present in the bacterium *Bacillus anthracis*. In order to enable detection, the substrate comprises a set of molecular markers that are used to detect a difference between the intact substrate and the substrate that is cleaved by the specific action of the *B. anthracis* protease.

Substrate for detection of micro-organisms, more specifically *B. anthracis*, wherein said substrate comprises a set of molecular markers linked with linkers to a di-, or tripeptide consisting of amino acids X1 and X2, or X1, X2 and X3, in which one of them, for example X1, is a D-amino acid and the others, for example X2 and X3, may be any D- or L-amino acid.

Central in the substrate is a sequence of two or three amino acids comprised of either one D-amino acid, which is preferably a neutral amino acid such as leucin, isoleucin, valine, glycine or alanine, more preferably leucine, isoleucine or valine, in combination with another D- or L-amino acid(s), preferably L-leucine, in either direction (i.e. Leu-DLeu or DLeu-Leu), to which the set of molecular markers is linked, optionally through a linker molecule. It has appeared that these sequences are very specifically cleaved by a hitherto unknown enzyme of *B. anthracis*. As can be seen in the experimental part, the substrate is specific in that it is hardly cleaved by closely related bacteria (*B. thuringiensis* and *B. cereus*) and not at all by *B. globigii*, *B. suis*, *E. coli* and *S. typhimurium*.

Also, these sequences seem to be specific in the sense that a change therein causes loss of the specific characteristics. As can be seen in the experimental part, a sequence with Leu-Leu is not cleaved by *B. anthracis*, but is cleaved by some other bacteria (*V. cholerae, P. aeruginosa, E. herbicola, C. botulinum* and *B. globigii*).

The di-/tripeptide that is preferred is the dipeptide Leu-DLeu (or the reverse (DLeu-Leu). It appears that this sequence is not only the best performing di-/tripeptide for the detection of *B. anthracis*, but that it can also be used for the ex vivo diagnosis of anthrax.

The molecular markers linked to the dipeptide of the invention may be any set of markers which can discriminate between the intact molecule and the cleaved molecule. A simple detection method may be e.g. mass spectrography in which the mass of the fragments is easily discriminated from the mass of the intact molecule. In such an assay, it is also unnecessary to have two molecular markers, since the presence of a marker at one side of the molecule will be sufficient for the detection.

If necessary, the molecular markers may be linked to the di- or tripeptide through linker molecules or linker moieties.

Preferred is an assay in which the presence of the cleaved peptide will be directly visible, such as by fluorescence. Especially advantageous is an assay that is based on the FRET technology. In such an assay a fluorophore is attached to one side of the molecule to be cleaved and a quencher for said fluorophore is attached to the other side of the molecule, but at a distance that the quencher is still able to quench the fluorophore in the intact molecule. Normally in FRET systems the distance between the fluorophore and the quencher may not exceed 100 Å. The choice of the fluorophore-quencher pair may be made from several available pairs, see e.g. Marras, S. A. E. (Meth. Mol. Biol. 335:3-16, 2006), where in table 2, 3 and 4 several fluorophores and their quenchers have been mentioned. These fluorophores and quenchers can all be used in the present invention. Preferably, FITC (fluorescein-5-isothiocyanate) is used as fluorophore and DABCYL (Dbc, 4-((-4-( )imethylamino)-phenyl)-azo)-benzoic acid) is used as the corresponding quencher.

The substrate flanked by the fluorophore-quencher pair would then be depicted as:

```
Marker1-(linker)-X1-X2-(linker)-Marker2
or
Marker1-(linker)-X1-X2-X3-(linker)-Marker2
``` in which one of X1, X2 or X3, for example X1, is a D-amino acid and the others, for example X2 and X3, may be any D- or L-amino acid In case the fluorophore-quencher pair is FITC and DABCYL, the formula will be represented by:

```
FITC-Ahx-X1-X2-(X3)-Lys-DABCYL,
``` in which X1, X2 and X3 are as defined above, the linker molecule Ahx is aminohexanoic acid, the linker molecule Lys is the amino acid lysine.

In the FRET assay, the substrate according to the invention is added to the sample and fluorescence will indicate that the fluorophore is no longer quenched by the quencher, which means that the substrate has been cleaved, which means that *B. anthracis* is present in the sample. Thus, this is a simple assay, with direct visual read-out of the presence or absence of anthrax in the sample. Detection of fluorescence can take place in the medium (on basis of the presence of the excreted proteolytic enzyme from *B. cereus*), but it has also proven feasible to detect the micro-organism itself. It appears from our experimental results that the substrate proteins of the invention are taken up by the bacteria and cleaved intracellulary, thereby generating fluorescence in the cell. Thus, the assay of the present invention can also be used to fluorescently stain viable *B. cereus* cells.

Alternatively, visible detection of protease activity can be performed through a novel assay based on color changes of gold colloids by cysteinyl derivatives (see: Guarise, C. et al., Proc. Natl. Acad. Sci. 103:3978-82, 2006). In this assay, the ability of a peptide having two terminal acetylated cysteines to interfere with the aggregation of nanometer-sized gold colloids and thereby introducing a shift in visible color, versus the lack of ability to introduce a color change of a peptide with only one such an acetylated cysteine terminal is used. The substrate of the present invention for such an assay would then be:

```
AcNH-Cys(S-Ac)-X1-X2-Cys(S-Ac)-OH
or
AcNH-Cys(S-Ac)-X1-X2-X3-Cys(S-Ac)-OH
``` in which X1, X2 and X3 are defined as above.

In this assay, the substrate is added to the sample and then the total of sample and substrate is added to a suspension of gold nanoparticles. If the color of the gold nanoparticles changes, then intact substrate is still available, meaning that the substrate has not been cleaved, which indicates that no *B. anthracis* has been present in the sample. No color change indicates a cleaved substrate and presence of anthrax.

The detection method of the invention is suitable for the detection of *B. anthracis*, but also other micro-organisms can be detected, as is shown in the examples, in several kinds of samples. Most preferable, a sample from a patient suspected of anthrax is used. Such a sample can be a blood, serum or plasma sample or can be derived from other body fluids, such as urine, sputum, lymph fluid, etc.

Alternatively, the sample can be taken from an environmental source, such as soil, water or air. In the latter case, preferably a filter is used through which the air is ventilated and in which the micro-organisms are collected. It is also possible, of course, to take a sample from any suspected powder (such as a powder in an envelope in the mail), from food that may be contaminated with anthrax or from medium in which micro-organisms are normally grown. After the sample is taken, it may be directly reacted with a substrate of the invention and fluorescence or other visual signal may be detected in *B. anthracis* is present. In this way a rapid diagnosis of the presence of anthrax may be obtained.

It has further appeared that the enzymatic activity from *B. anthracis* that is responsible for cleavage of the dipeptide is resided on the PXO1 plasmid. Since this plasmid also harbours the toxicity genes of anthrax, such as the lethal factor protein, the present method of detection is also specific for those strains of *B. anthracis* that are harmful. Hence, it is also possible with the present detection method to identify *B. anthracis*$^{PXO1+}$ strains.

During the development of a FRET substrate for the detection and diagnosis of *B. anthracis* another substrate, BikKam21, appeared to be specific in the detection of *P. aeruginosa* (FIG. 3J). To get more insight in the working mechanism of this substrate, BikKam21 analogs were designed denoted by BikKam20 to BikKam24 (Table 1). Adding or removing one glycine (BikKam20 and BikKam22) led to an increase in cleavage of the substrate by *P. aeruginosa* (FIG. 6A-C). However, in case more glycines were removed from the substrate sequence (BikKam23) a significant decrease in activity was observed (FIG. 6D). The BikKam21 analog with only one glycine (BikKam24) showed no *P. aeruginosa* activity (FIG. 6E).

Cleavage of the *P. aeruginosa* substrates is probably due to LasA, an enzyme which is important in the virulence of *P. aeruginosa*. Besides LasA, the peptide sequence of BikKam20 and Bikam2l is also recognized by the bacterial enzyme lysostaphin. Therefore the specificity of the BikKam21 substrate and its analogs was checked using lysostaphin (Sigma) and culture supernatants of lysostaphin producing bacteria like *Streptococcus equi zooepidemicus*. BikKam20 and BikKam21 were cleaved by lysostaphin. Shortening the substrate to three glycins led to an increase in *P. aeruginosa* activity and a decrease in lysostaphin activity (FIG. 6C). BikKam23 had lower activity for *P. aeruginosa* but was not cleaved by lysostaphin (FIG. 6D).

Unless some of the described substrates were cleaved by purified lysostaphin, none of the lysostaphin producing bacteria was able to cleave the BikKam-substrates (FIG. 6). In conclusion the FRET substrates BikKam21 to BikKam23 can be used in the detection and diagnosis of *P. aeruginosa*, whereas BikKam23 is the most preferred since it does not interact with lysostaphin.

EXAMPLES

Example 1

Materials and Methods

Bacteria

Bacteria were grown overnight in Brain Heart Infusion (BHI) medium or 70% Human serum (HuS) at the appropriate growth temperature. Next day the bacteria were pelleted by centrifugation for 10 min at 10 000 rpm. Supernatant was sterilized by filtration through an 0.22 uM filter (MilliPore). For mass spectrometric analysis and confirmation of the in vitro and ex vivo results sera of mice that were suffering a *B. anthrax* infection was filtrated on a Waters Sep-Pak classic cartridge WAT051910 C18 column.

Reagents

FRET peptides were synthesized by PepScan (The Netherlands). Identity and purity were verified by mass spectrometry and reverse phase HPLC. Anthrax Lethal Factor (LF) was purchased from List Laboratories. Thermolysin, Collagenase *Clostridium* and lysostaphin were purchased from Sigma. Collagenase *Vibrio*/Dispase was purchase from Roche. LF inhibitor 12155 was synthesized by Pyxis (The Netherlands). Nine experimental peptides were synthesized and reacted with FITC and DABCYL to form the following reagents:

| Internal code | Formula |
|---|---|
| BikKam 1 | FITC-Ahx-Leu-DLeu-Lys-DABCYL |
| BikKam 2 | FITC-Ahx-DLeu-Leu-Lys-DABCYL |
| BikKam 3 | FITC-Ahx-Leu-Leu-Lys-DABCYL |
| BikKam 4 | FITC-Ahx-DLeu-DLeu-Lys-DABCYL |
| BikKam 5 | FITC-Ahx-Leu-DLeu-Leu-Lys-DABCYL |
| BikKam 6 | FITC-Ahx-Leu-DVal-Lys-DABCYL |
| BikKam 7 | FITC-Ahx-Gly-DLeu-Lys-DABCYL |
| BikKam 8 | FITC-Ahx-Gly-DAla-Lys-DABCYL |
| BikKam 9 | FITC-Ahx-Pro-Hyp-Lys-DABCYL |
| BikKam 20 | FITC-Ahx-Gly-Gly-Gly-Gly-Gly-DABCYL |
| BikKam 21 | FITC-Ahx-Gly-Gly-Gly-Gly-DABCYL |
| BikKam 22 | FITC-Ahx-Gly-Gly-Gly-DABCYL |
| BikKam 23 | FITC-Ahx-Gly-Gly-DABCYL |
| BikKam 24 | FITC-Ahx-Gly-DABCYL |

Ahx = aminohexanoic acid, Leu = L-leucine, DLeu = D-leucine, Lys = L-lysine, DVal = D-valine, Gly = L-glycine, DAla = D-alanine, Pro = L-proline, Hyp = hydroxyproline.

FRET Assay

Assay reactions were preformed in blackwell, clear bottom 96-well plates (Corning). For the enzyme assay 10 uM of each of the above mentioned reagents was incubated at 37° C. in presence of Thermolysin (1 ug), Collagenase *Clostridium* (10 ug), Collagenase *Vibrio*/Dispase (5 ug) or LF (1 ug). Enzyme activity in bacterial supernatants was determined by incubating 16 uM FRET peptide with 100 uL filtered supernatant at 37° C. Filtered BHI medium or 70% HuS was used as control. Plates were read with 10 min intervals on a Cytofluor 4000 (Applied Biosystems) with excitation using a 485 nm filter and emission using a 530 nm filter. The results are shown in FIGS. 1, 2 and 3.

Mass Spectrometry

SepPak fractions (Waters Sep-pak classic cartridge C18) of BikKam1 1): in BHI with and without *B. antracis*; and 2): incubated with serum of an infected and control mice were analyzed for the presence of [FITC]-Ahx-Leu-D-Leu and [dabcyl]-K($NH_2$).

These samples were analysed with ES-LC-MS/MS under the following conditions:

| Elution liquid A: H₂O (0.2% formic acid) | | Elution liquid B: CH₃CN (0.2% formic acid) | |
|---|---|---|---|
| Gradient: | time (min.) | % A | % B | flow (ml/min.) |
| | 0 | 100 | 0 | 0.6 |
| | 45 | 10 | 90 | 0.6 |

The flow of 0.6 ml/min. was reduced by an LC-packings splitter to about 40 µl/min.

| Column: PepMap C₁₈; 3 µm; 15 cm × 1 mm | Size: 10 en 50 µl |
|---|---|

Spectra (MS/MS) of the produced ions were recorded from the double charged molecular ion (MH$_2^{2+}$ 199.1) of [dabcyl]-K(NH₂) with a cone voltage of 20 V and a collision energy of 10-11 eV. Spectra were recorded from the double charged molecular ion (MH$_2^{2+}$ 374.2) of [FITC]-Ahx-Leu-D-Leu with a cone voltage of 20-25 V and a collision energy of 13 eV.

The argon gas pressure was 10⁻⁴ mBar.

Figure 4A:
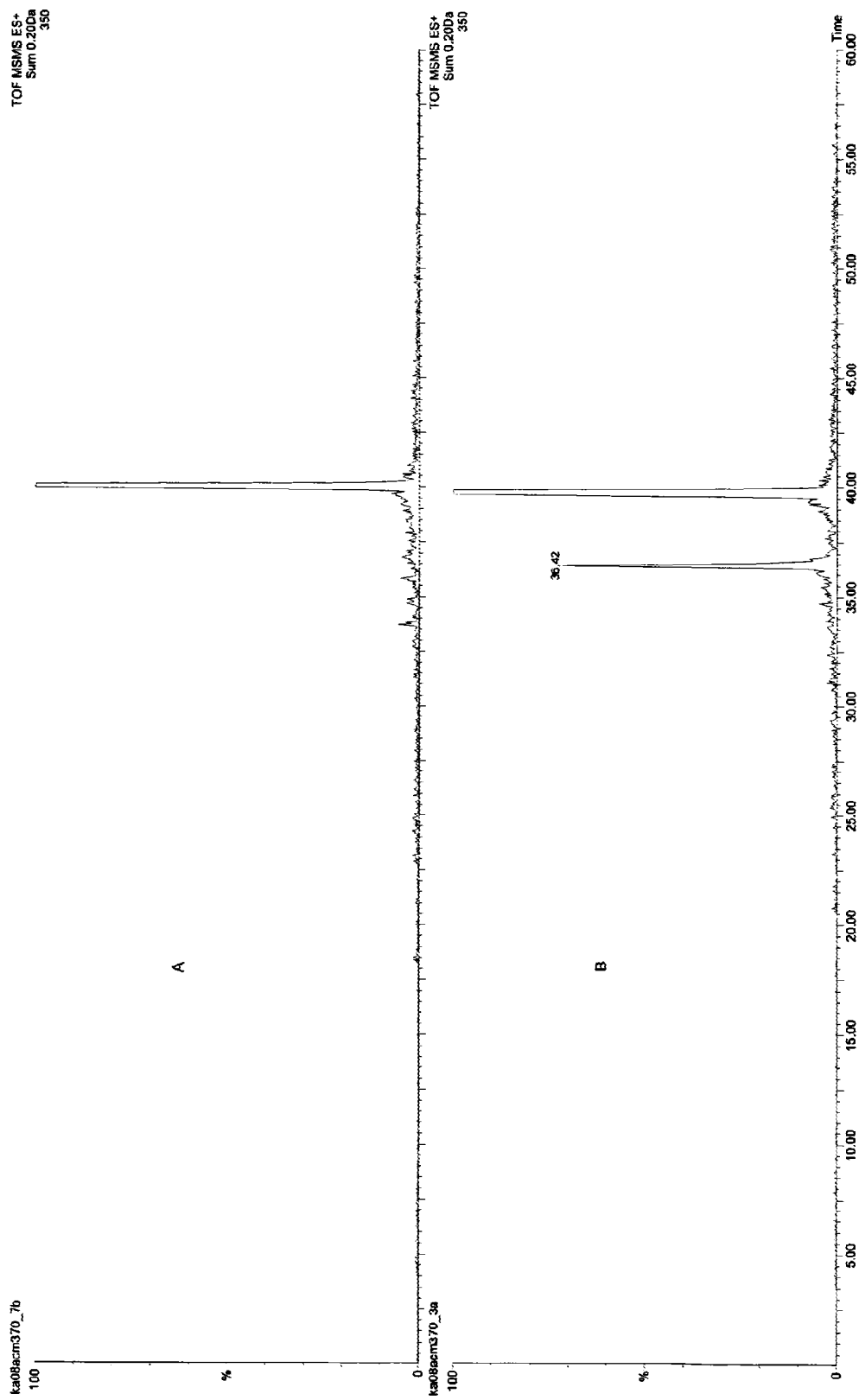
FIG. 4. A: Extracted ion chromatograms of ions m/z 132.1+348.1+390.1+503.2+616.2, fragments in the product ion mass spectrum of $MH_2^{2+}$+374.2 of [FITC]-Ahx-Leu-D-Leu. Upper panel: serum of uninfected mouse, lower panel: serum of infected mouse.
B: product ion mass spectra of $MH_2^{2+}$ 374.2 of [FITC]-Ahx-Leu-D-Leu.
Figure 4B:
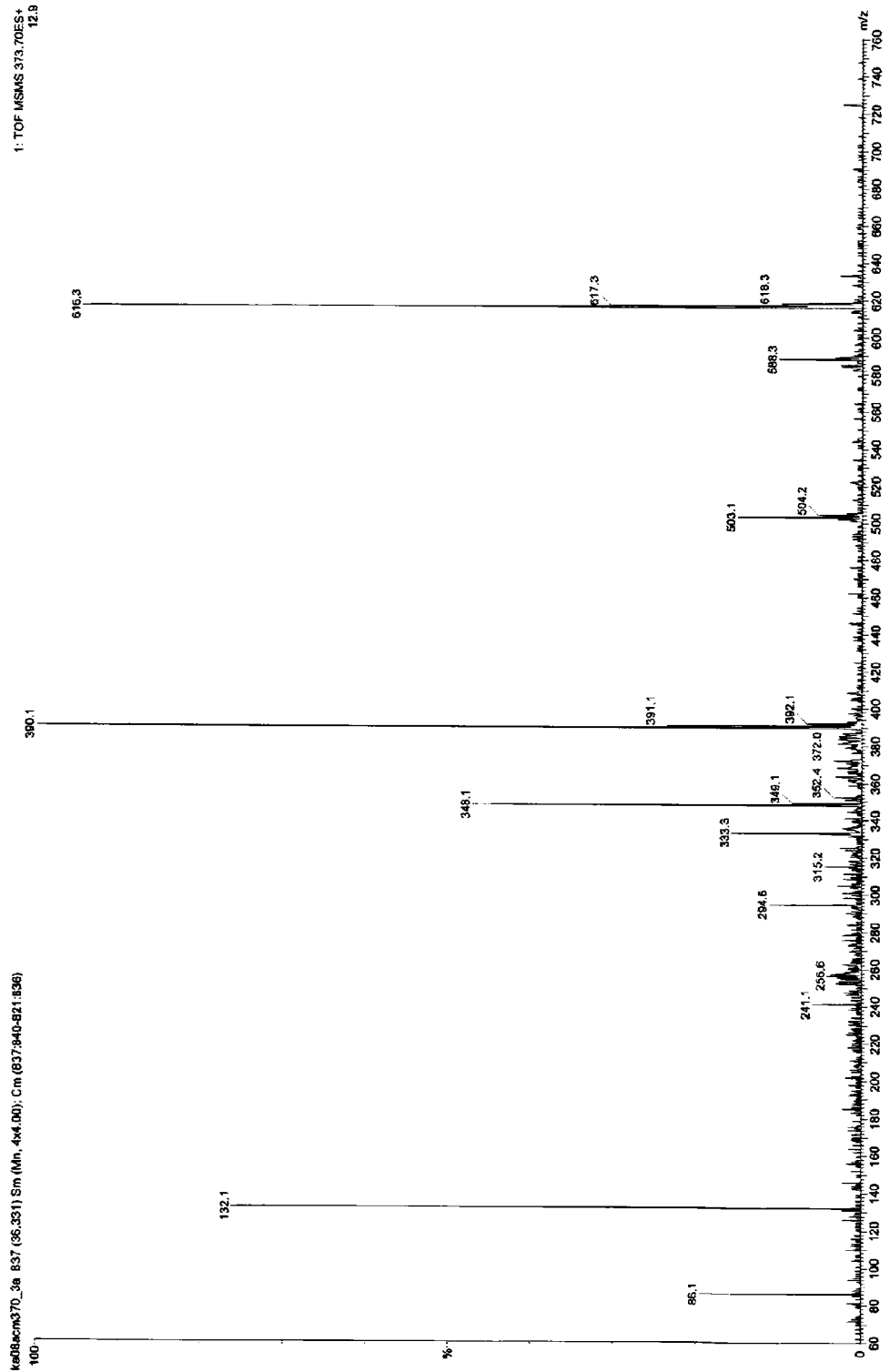

The results in FIG. 4 show that compared to uninfected mice (FIG. 4A) in *B. anthracis* infected mice an additional peak is observed, representing in this example [FITC]-Ahx-Leu-D-Leu.

Example 2

Material and Methods

*B. cereus* and *B. globigii* cells were grown overnight in 5 ml BHI medium at 37° C. Next day the bacteria were diluted 1:10 in BHI and grown in presence of 0.01 M BikKam1 (PepScan, The Netherlands). During growth, cell samples were taken with 1 hour time intervals. The cell samples were washed twice with PBS, reconstituted with 20 uL PBS and spotted onto glass slides. As a negative control bacteria grown for 16 hr without BikKam1 were used. Fluorescence microscopy was performed with a Leitz Orthoplan microscope using a 1000 fold magnification.

Results

Figure 5:
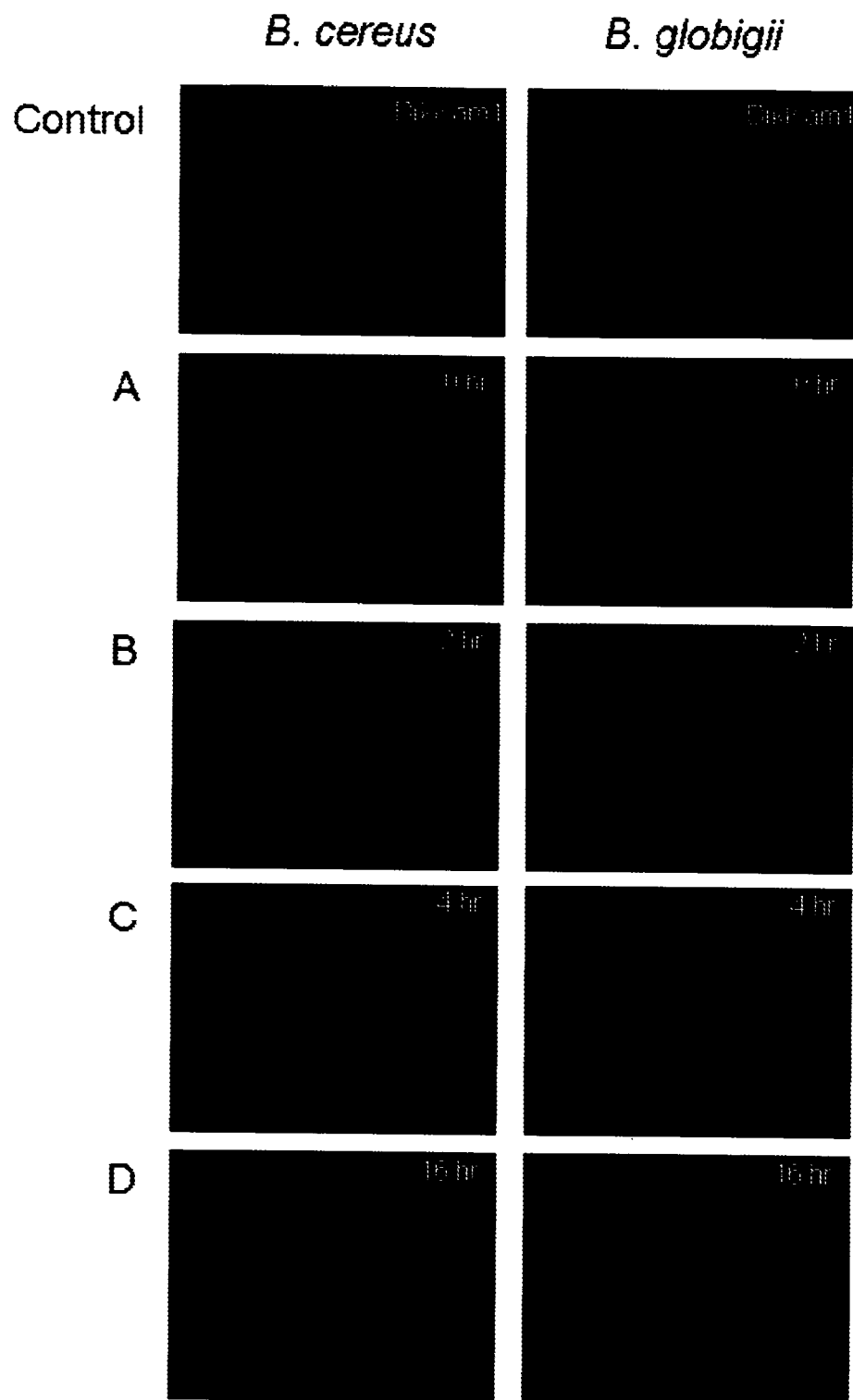
FIG. 5. Detection of fluorescent BikKam1 fragments in the cytoplasm of *B. cereus*. For details, see text.
Figure 6A:
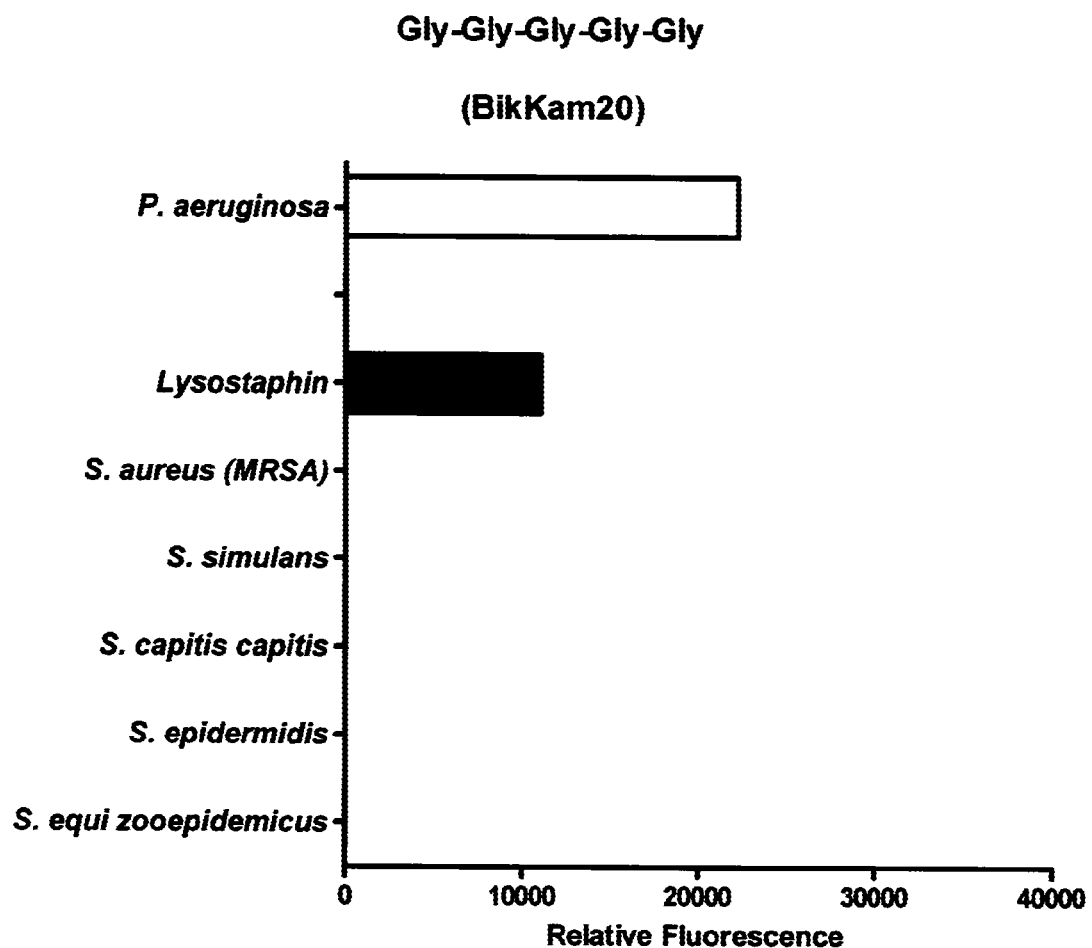
FIG. 6 Fluorescent signal of FRET after 60 minutes of invented *P. aeruginosa* substrates by enzymes of bacteria grown in bacterial growth medium (BHI) (in vitro)
A: BikKam20 is specifically cleaved by a *P. aeruginosa*-derived enzyme and lysostaphin.
B: BikKam21 is specifically cleaved by a *P. aeruginosa*-derived enzyme and lysostaphin. Compared to BikKam20 a slight increase in activity for *P. aeruginosa* is observed
C: BikKam22 is specifically cleaved by a *P. aeruginosa*-derived enzyme. Also somewhat cleavage by lysostaphin could be detected. Compared to BikKam20 and BikKam21 a slight increase in activity for *P. aeruginosa* is observed.
D: BikKam23 is specifically cleaved by a *P. aeruginosa*-derived enzyme. The effectivity of this substrate is lower than BikKam20-BikKam22.
E. No significant enzyme activity could be measured using BikKam24 with the currently used micro-organisms and lysostaphin.
Figure 6B:
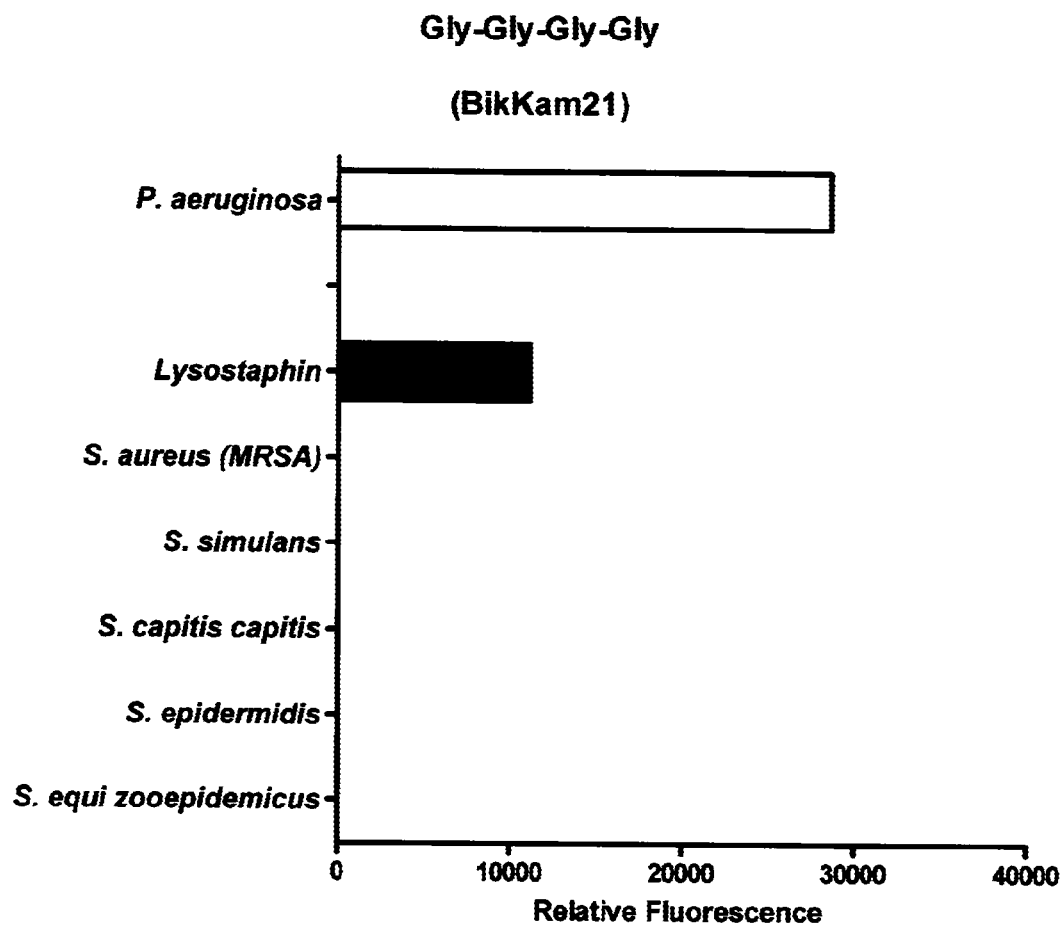
Figure 6C:
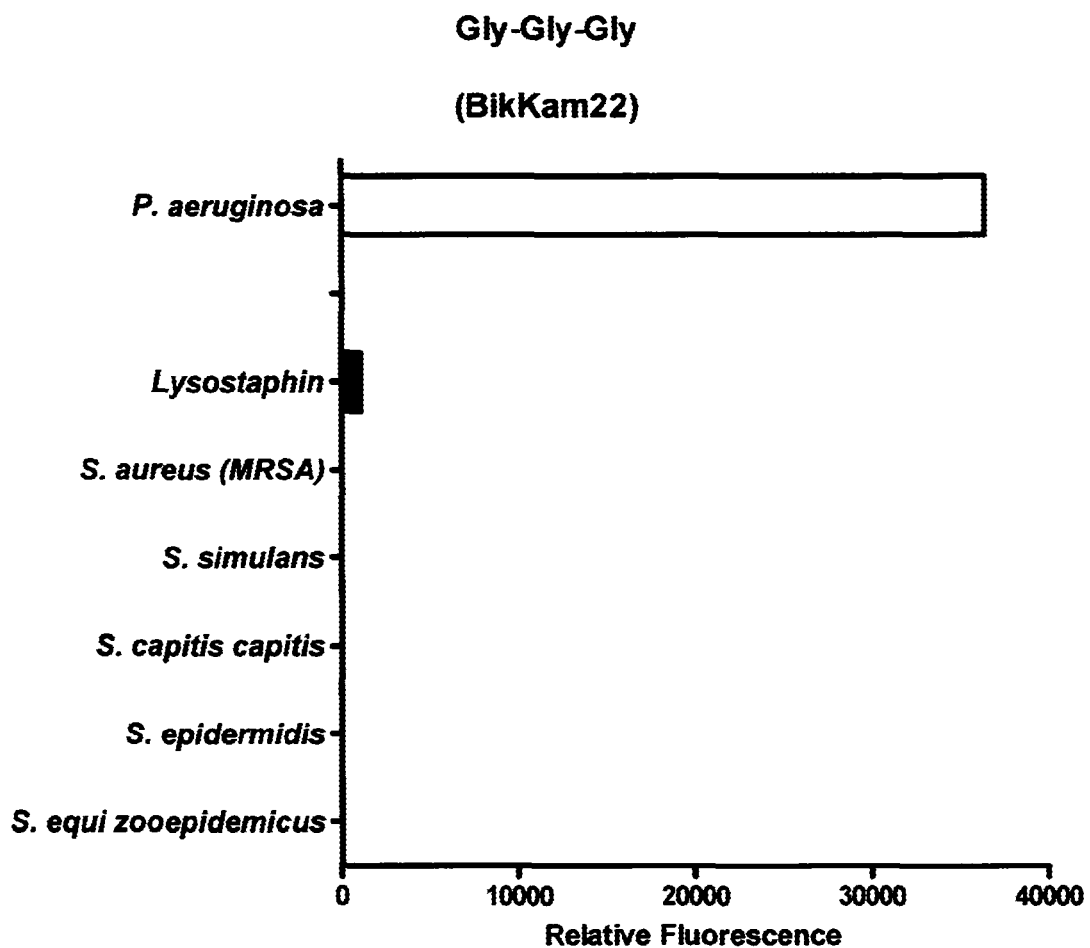
Figure 6D:
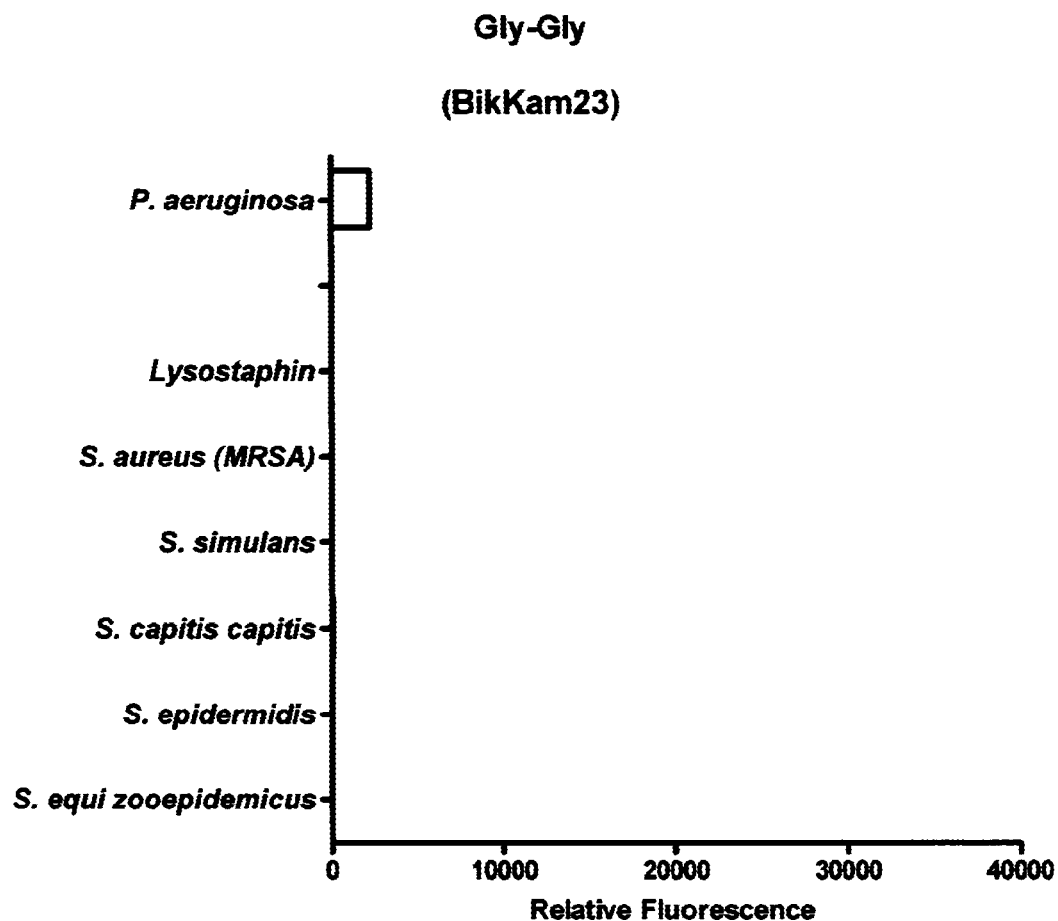
Figure 6E:
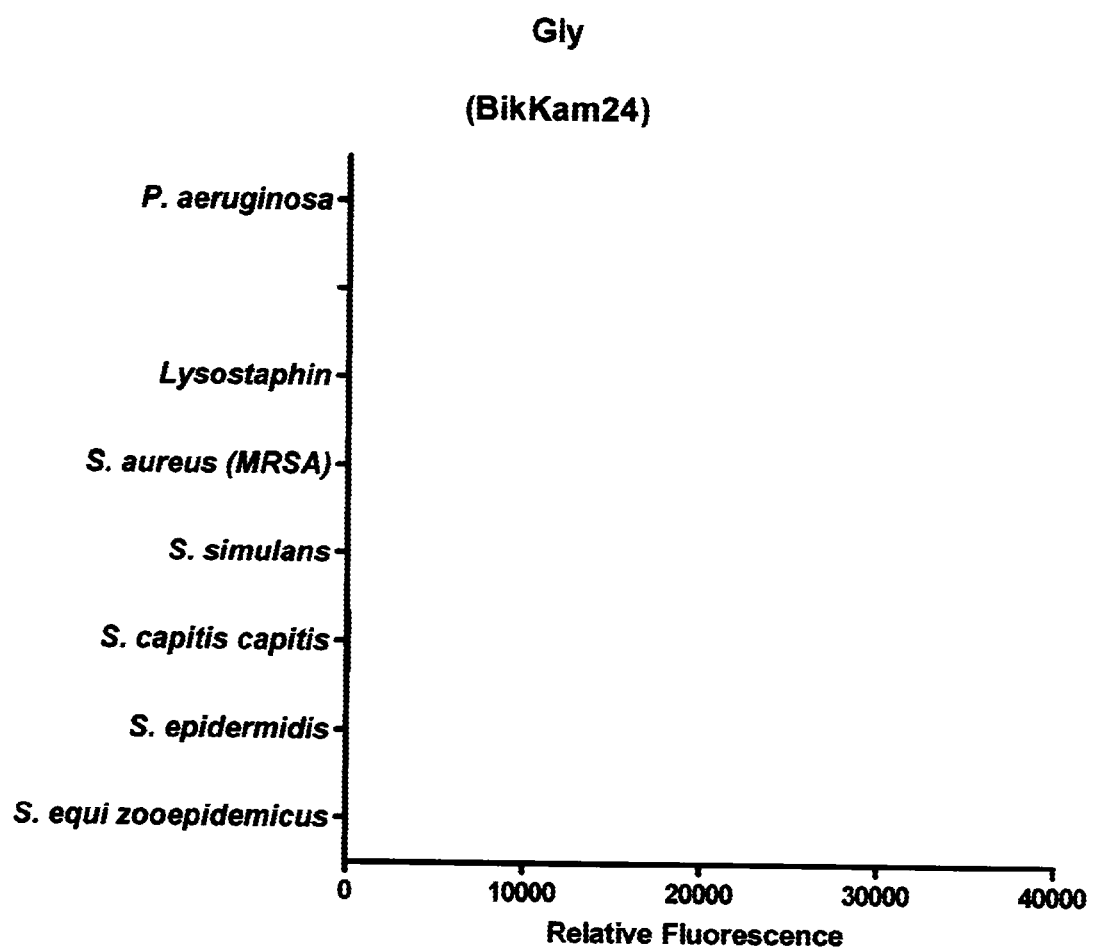

After 2 hr incubation, fluorescent BikKam1 fragments could be detected in the cytoplasm of *B. cereus* (FIG. 5B). At 4 hr, the fluorescent BikKam1 fragments were besides in the cytoplasm also present in the cell wall at the new division sides (the side wall) (FIG. 5C). Finally, after 16 hr incubation, all BikKam1 fragments were moved from the cytoplasm to the side walls of *B. cereus* (FIG. 5D). The bacterium *B. globigii* is not capable of cleaving the BikKam1 substrate and was therefore used as a negative control. As expected, culturing *B. globigii* in presence of BikKam1 did not lead to fluorescent bacteria. Also no fluorescent bacteria could be detected at 0 hr and in samples grown without BikKam1 (FIG. 5A). These results show that besides the previously described FRET assay, detection of bacteria enzymes, it is also possible to make bacteria visible using the BikKam1 substrate.

The invention claimed is:

1. A substrate for detection of *Bacillus anthracis*, wherein the substrate comprises FITC-Ahx-X1-X2-X3-Lys-DABCYL, wherein X1 is L-Leu, D-Leu, or Gly; X2 is L-Leu, D-Leu, or D-Val; X3 is L-Leu, D-Leu, or absent, Lys stands for Lysine, Ahx stands for aminohexanoic acid, FITC is fluorescein-5-isothiocyanate, DABCYL is 4-((-4-dimethylamino)-phenyl)-azo-) benzoic acid, and one of the amino acids is a D-amino acid and the others are D- or L-amino acids.

2. A substrate for detection of *Bacillus anthracis*, wherein the substrate comprises AcNH-Cys(S-Ac)-X1-X2-X3-Cys(S-Ac)-OH, wherein X1 is L-Leu, D-Leu, or Gly; X2 is L-Leu, D-Leu, or D-Val; X3 is L-Leu, D-Leu, or absent, Cys(S-Ac) stands for thiol acetylated cysteine and AcNH for an acetylated amino terminus, and one of the amino acids is a D-amino acid and the others are D- or L-amino acids.

3. The substrate of claim 1, wherein the substrate is selected from the group consisting of:

```
FITC-Ahx-Leu-DLeu-Lys-DABCYL,
FITC-Ahx-DLeu-Leu-Lys-DABCYL,
FITC-Ahx-DLeu-DLeu-Lys-DABCYL,
FITC-Ahx-Leu-DLeu-Leu-Lys-DABCYL,
FITC-Ahx-Leu-DVal-Lys-DABCYL,
and
FITC-Ahx-Gly-DLeu-Lys-DABCYL.
```

4. The substrate of claim 1 or claim 2, wherein the L-amino acid or one of the two L-amino acids is Leu.

5. The substrate of claim 2, wherein said substrate is:

```
AcNH-Cys(S-Ac)-X1-X2-X3-Cys(S-Ac)-OH,
``` wherein the L-amino acid or one of the two L-amino acids is Leu, wherein X3 may be absent, and wherein Cys(S-Ac) stands for thiol acetylated cysteine and AcNH for an acetylated amino terminus.

6. The substrate of claim 2, wherein the substrate is selected from the group consisting of:

```
AcNH-Cys(S-Ac)-Leu-DLeu-Cys(S-Ac)-OH,
AcNH-Cys(S-Ac)-DLeu-Leu-Cys(S-Ac)-OH,
AcNH-Cys(S-Ac)-DLeu-DLeu-Cys(S-Ac)-OH,
AcNH-Cys(S-Ac)-Leu-DLeu-Leu-Cys(S-Ac)-OH,
AcNH-Cys(S-Ac)-Leu-DVal-Cys(S-Ac)-OH,
and
AcNH-Cys(S-Ac)-Gly-DLeu-Cys(S-Ac)-OH.
```

7. The substrate of claim 1 or claim 2, wherein the D-amino acid is DLeu or DVal.

8. A method for the detection of *Bacillus anthracis* in a sample comprising adding the substrate of claim 1 or claim 2 to the sample and detecting a fluorescent signal or a shift in color.

9. The method of claim 8 wherein the fluorescent signal is located intracellularly in the microbial cells.

10. The method of claim 8, wherein the sample is selected from a body fluid, powder, water, food, medium, or any other biological matrix.

11. A method for the identification of *Bacillus anthracis*$^{PXO1+}$ in a sample comprising adding the substrate of claim 1 or claim 2 to the sample and detecting a fluorescent signal, a shift in color, a specific mass spectrum, or detection by capillary electrophoresis.

* * * * *